United States Patent [19]

Skuballa et al.

[11] Patent Number: 4,925,956
[45] Date of Patent: May 15, 1990

[54] PROCESS FOR MANUFACTURING OPTICALLY ACTIVE CARBACYCLIN INTERMEDIATES

[75] Inventors: Werner Skuballa; Helmut Dahl, both of Berlin, Fed. Rep. of Germany

[73] Assignee: Schering Aktiengesellschaft, Berlin and Berghamen, Fed. Rep. of Germany

[21] Appl. No.: 237,114
[22] PCT Filed: Nov. 12, 1987
[86] PCT No.: PCT/DE87/00515
§ 371 Date: Jul. 13, 1988
§ 102(e) Date: Jul. 13, 1988
[87] PCT Pub. No.: WO88/03526
PCT Pub. Date: May 19, 1988

[30] Foreign Application Priority Data

Nov. 13, 1986 [DE] Fed. Rep. of Germany ....... 3638757

[51] Int. Cl.$^5$ ............... C07D 319/08; C07C 177/00; C07C 47/575; C07F 7/18
[52] U.S. Cl. .................. 549/214; 549/421; 549/337; 549/336; 549/332; 556/436; 562/501; 568/445
[58] Field of Search ............... 549/336, 337, 421, 214, 549/332; 568/445; 556/436; 562/501

[56] References Cited

U.S. PATENT DOCUMENTS 3,891,676 6/1975 Kuo et al. ............... 549/311

OTHER PUBLICATIONS

Mukaiyama et al., Chem. Lett., No. 3, 1983, pp. 385–388.

Primary Examiner—Nicky Chan
Attorney, Agent, or Firm—Millen, White & Zelano

[57] ABSTRACT

The invention relates to a process for manufacturing optically active carbacyclin intermediate products from racemic cis-bicyclo[3.3.0]octane-2-carboxylic acids. This process makes it possible in an advantageous way to produce important intermediates for the synthesis of stable and pharmacologically active carbacyclin derivatives.

7 Claims, No Drawings

NOVEL PROCESS FOR MANUFACTURING OPTICALLY ACTIVE CARBACYCLIN INTERMEDIATES

The various possibilities of synthetizing carbacyclin analogs are compiled in the two following articles of an overview nature: R. C. Nickolson, M. H. Town and H. Vorbrüggen, "Medicinal Research Review" 5: 1 (1985); P. A. Aristoff in "Advances in Prostaglandin, Thromboxane and Leukotriene Research" 15 (1985). Heretofore, all known synthesis methods for pure, optically active carbacyclins have been accompanied by considerable expense for the synthesis. Thus, carbacyclin syntheses have been described, for example, in DOS 2,912,409 and DOS 3,021,895 which make it possible to obtain, from the optically active "Corey lactone", a conversion into carbacyclin intermediates only under great losses in yield.

It has now been found that the diastereomeric amides of Formula II, formed from D-(—)-α-phenylglycinol and racemic cis-bicyclo[3.3.0]octane-2-carboxylic acids, surprisingly can be separated with special ease and therefore are suitable, after reductive splitting of the amide, for the production of the pure, optically active carbacyclin intermediates of Formula I.

The invention accordingly concerns a process for the manufacture of optically active cis-bicyclo-[3.3.0]octane-2-aldehydes of Formula I

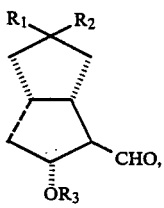

(I)

wherein $R_1$ and $R_2$ jointly represent the double-linkage residue —O—X—O— where X is straight-chain or branched-chain alkylene of 1-7 carbon atoms, or $R_1$ and $R_2$ individually represent the residue OR where R is straight-chain or branched-chain alkyl of 1-7 carbon atoms, and $R_3$ is hydrogen, a saturated alkyl residue of 1-7 carbon atoms, an aralkyl residue of 7-10 carbon atoms, a tetrahydropyranyl residue, a trialkylsilyl residue of 1-6 carbon atoms in the alkyl, wherein alkyl can also be substituted by phenyl, a dialkylphenylsilyl residue or an alkyldiphenylsilyl residue of 1-16 carbon atoms in the alkyl, characterized in that the diastereomeric amides of Formula II

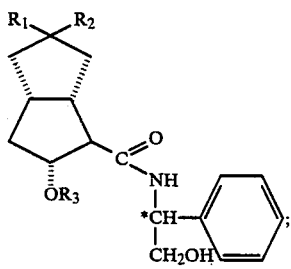

(II)

wherein $R_1$, $R_2$ and $R_3$ have the meanings set forth above, are separated and the enantiomerically pure amide of Formula II is reduced.

If X represents a straight-chain or branched-chain alkylene residue of 1-7 carbon atoms, then the following residues are meant:

—$(CH_2)_n$— wherein n=1-7 (methylene, ethylene, tri-, tetra-, penta-, hexa- and heptamethylene), —$C(CH_3)_2$—, —$CH(CH_3)$—, —$CH((CH_3)$—$CH_2$—, —$C(CH_3)_2$—$CH_2$—, —$CH_2$—$CH(CH_3)$—, $CH_2$—$C(CH_3)_2$, —$CH_2$—$CH(CH_3)$—$CH_2$—, —$CH_2$—$C(CH_3)_2$—$CH_2$—, —$CH$—$(C_2H_5)$—, —$C(C_2H_5)_2$—, —$CH(C_2H_5)$—$CH_2$—, —$C(C_2H_5)_2$—$CH_2$—, —$CH_2$—$CH(C_2H_5)$—, —$CH_2$—$C(C_2H_5)_2$—, —$CH_2$—$CH(C_2H_5)$—$CH_2$—, —$CH_2$—$C(C_2H_5)_2$—$CH_2$— etc.

R, as a straight-chain or branched-chain alkyl residue of 1-7 carbon atoms, means methyl, ethyl, n-propyl, isopropyl, n-butyl, isobutyl, sec-butyl, tert-butyl, n-pentyl, isopentyl, sec-pentyl, neopentyl, n-hexyl, isohexyl, n-heptyl, isoheptyl.

$R_3$ and, respectively, $R_4$ (in Formula IV) as saturated alkyl residues of 1-7 carbon atoms mean the alkyl residues already recited for R.

$R_3$ and, respectively, $R_4$ as aralkyl residues of 7-10 carbon atoms are to encompass the following residues:

—$CH_2$—$C_6H_5$, —$CH_2$—$CH_2$—$C_6H_5$,

—$CH_2$—$CH_2$—$CH_2$—$C_6H_5$, —$CH_2$—$CH_2$—$CH_2$—$CH_2$—$C_6H_5$,

—$\underset{\underset{CH_3}{|}}{CH}$—$C_6H_5$, —$CH_2$—$\underset{\underset{CH_3}{|}}{CH}$—$C_6H_5$, —$CH_2$—$CH_2$—$\underset{\underset{CH_3}{|}}{CH}$—$C_6H_5$, —$\underset{\underset{CH_3}{|}}{CH}$—$CH_2$—$C_6H_5$, —$\underset{\underset{CH_3}{|}}{CH}$—$CH_2$—$CH_2$—$C_6H_5$, —$CH_2$—$\underset{\underset{CH_3}{|}}{CH}$—$CH_2$—$C_6H_5$, —$\underset{\underset{C_2H_5}{|}}{CH}$—$C_6H_5$, —$CH_2$—$\underset{\underset{C_2H_5}{|}}{CH}$—$C_6H_5$, —$\underset{\underset{C_3H_7}{|}}{CH}$—$C_6H_5$, —$C(CH_3)_2$—$C_6H_5$, —$CH_2$—$C(CH_3)_2$—$C_6H_5$, —$\underset{\underset{CH_3CH_3}{|}}{CH}$—$CH$—$C_6H_5$, —$C(CH_3)_2$—$CH_2$—$C_6H_5$ etc.

The residues recited above for R are suitable for the "alkyl" residues in trialkyl- (of 1-6 carbon atoms in the alkyl), dialkylphenyl-, or alkyldiphenylsilyl of 1-16 carbon atoms in the alkyl.

The compounds of Formula I are especially suited as intermediates for the preparation of stable, pharmacologically effective carbacyclin derivatives (e.g. iloprost).

The amides of Formula II are prepared according to the methods known to persons skilled in the art. For example, the diastereomeric amides of Formula II can be produced by reacting the racemic carboxylic acids of Formula III

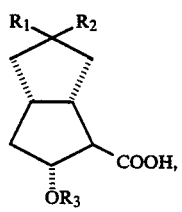

(III)

wherein $R_1$, $R_2$ and $R_3$ have the meanings indicated above, with a base, preferably triethylamine, and the isobutyl ester of chloroformic acid to obtain the intermediate anhydride, and by subsequent addition of D-(—)-α-phenylglycinol. The reaction is performed at −20° C. to 80° C., preferably at 0° C. to 30° C., in an inert solvent. Examples of suitable solvents are acetone, acetonitrile, methylene chloride, ethylene chloride, and others. The separation of the diastereomeric amides can take place in a simple way by column chromatography on silica gel or aluminum oxide or by fractional crystallization.

Diisobutyl aluminum hydride can serve, for example, as the reducing agent for the amide cleavage. The reductive splitting of the amide is conducted at −120° C. to 30° C., preferably −70° C. to 0° C. Suitable solvents or solvent mixtures are, for example, toluene, tetrahydrofuran, diethyl ether, methylene chloride, ethylene chloride, etc.

The starting material of Formula III required for the process of this invention can be produced by selective ketalization of the known cis-bicyclo[3.3.0]-octane-3,7-dione with an alcohol or diol

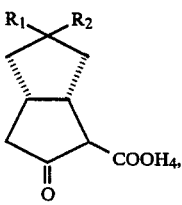

(IV)

corresponding to the meaning of $R_1$ and $R_2$. The starting material of Formula III is obtained by introduction of the COOR$_4$ group by reaction, for example, with bases and dialkyl carbonates to the compound of Formula IV wherein $R_4$ stands for alkyl of 1–7 carbon atoms or aralkyl of 7–10 carbon atoms, as well as subsequent reduction of the keto group with sodium borohydride and optionally blockage of the thus-formed hydroxy group, for example by silylation with tert-butyldimethylsilyl chloride, and saponification of the ester group. The further conversion of the compounds of Formula I into the pharmacologically active carbacyclin derivatives takes place according to a conventional procedure, for example by condensation with 3-methyl-2-oxohept-5-ynephosphonic acid dimethyl ester and sodium hydride to the α,β-unsaturated ketone 5. Reduction of ketone 5 to the alcohol 6, subsequent blocking group cleavage to the diol 7, and formation of tetrahydropyranyl ether yields the ketone 8 which is converted, after Wittig reaction with the ylene from 4-carboxybutyltriphenylphosphonium bromide and subsequent cleavage of blocking groups with aqueous acetic acid, into the carbacyclin derivative iloprost.

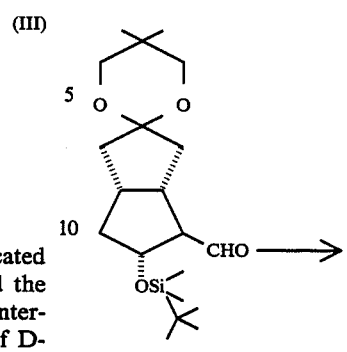

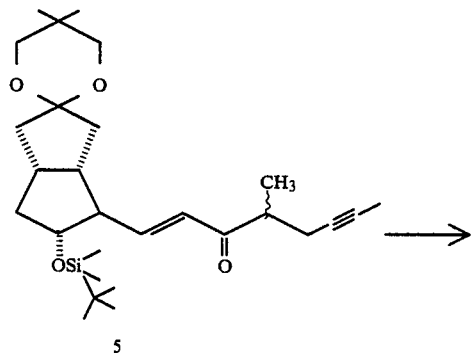

5

I ($R_1$ and $R_2$ = —O—CH$_2$—C(CH$_3$)$_2$—O—, $R_3$ = dimethyl tert-butylsilyl)

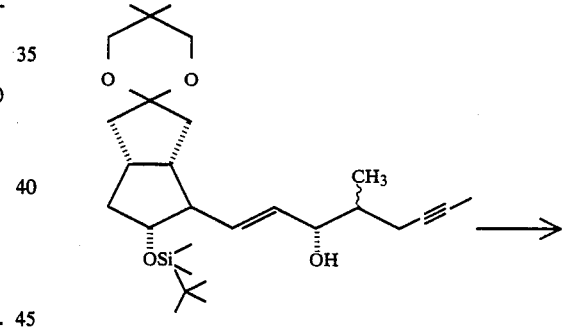

6

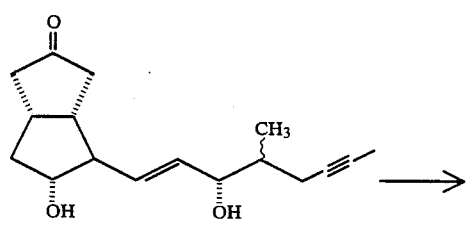

7

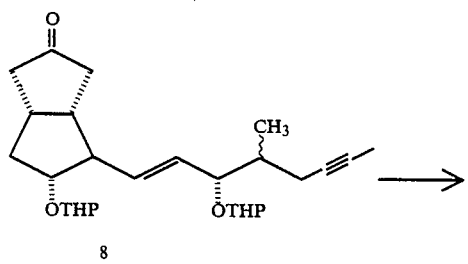

8

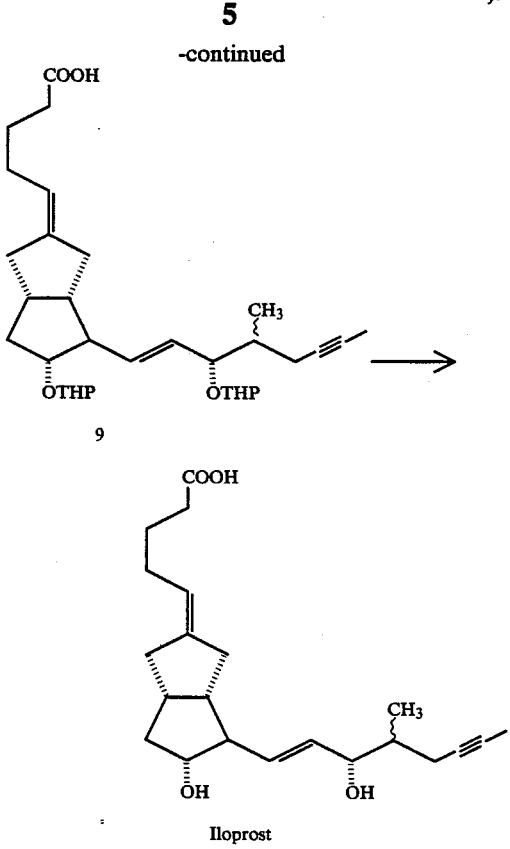

Iloprost

EXAMPLE 1

7,7-(2,2-Dimethyltrimethylenedioxy)-2β-formyl-3α-(tert-butyldimethylsilyloxy)-cis-bicyclo[3.3.0]octane At 0° C., 2.08 ml of triethylamine is added to a solution of 4.8 g of 7,7-(2,2-dimethyltrimethylenedioxy)-3α-(tert-butyldimethylsilyloxy)-cis-bicyclo[3.3.0]octane-2β-carboxylic acid in 55.6 ml of acetone; the mixture is stirred for 5 minutes, combined with a solution of 1.92 ml of the isobutyl ester of chloroformic acid in 35 ml of acetone, and agitated for 20 minutes at 0° C. Then a solution of 1.88 g of D-(−)-α-phenylglycinol in 17 ml of acetone and 17 ml of acetonitrile is added dropwise and the mixture is stirred for 24 hours at 25° C., concentrated under vacuum, taken up in 200 ml of methylene chloride, shaken with brine, dried over magnesium sulfate, and evaporated under vacuum. The residue is separated by column chromatography on silica gel with ethyl acetate/hexane (6:4), thus obtaining, as a nonpolar compound, after recrystallization from toluene, 2.7 g of the D-(−)-α-phenylglycinolamide having the absolute configuration represented by general Formula II (melting point 157°–159° C.).

$([α]_D = -25.9°$ (c=0.54 in $CHCl_3$).)

After further elution with EtOAc/hexane (1:1), evaporation, and subsequent recrystallization from toluene, 2.25 g of the correspondingly mirror-image configured D-(−)-α-phenylglycinolamide is obtained as the polar component (melting point 148°–149° C.).

$([α]_D = -9.3°$ (c=0.32 in $CHCl_3$).)

In addition, mixed fractions are also obtained which can be readily separated by repeated chromatography or fractional crystallization.

The correlation of the absolute configurations is effected by comparison of melting point, by NMR and by thin layer comparison of the amides obtained after ketal splitting and silyl ether cleavage with the corresponding amide synthesized from intermediates of a known absolute configuration for comparison purposes.

For the reductive amide cleavage to obtain the aldehyde of general Formula I, 1.5 g of the above-obtained, nonpolar D-(−)-α-phenylglycinolamide is dissolved in 20 ml of methylene chloride and gradually 12.3 ml of a 14.8-molar solution of diisobutyl aluminum hydride in toluene is added dropwise thereto. The mixture is stirred for one hour at −70° C., 4 ml of isopropanol is added dropwise, 4 ml of water is added, the mixture is diluted with 10 ml of methylene chloride, stirred for one hour at 25° C., filtered, and evaporated under vacuum. The residue is purified by column chromatography on silica gel. With ethyl acetate-hexane (3+2), 444 mg of the title compound is obtained as a colorless oil.

IR ($CHCl_3$): 2960, 2860, 2720, 1719, 840 $cm^{-1}$.

The rotation value is $[α]_D^{20} -23.6°$ (c=0.95 in $CHCl_3$).

In addition, 530 mg of the unreacted starting amide is also isolated.

The starting material for the above title compound was prepared as follows:

1(a)

(2,2-Dimethyltrimethylenedioxy)-cis-bicyclo[3.3.0]octan-3-one-2-carboxylic Acid Methyl Ester A suspension is prepared from 38.34 g of 55–60% strength sodium hydride in 616 ml of dimethyl carbonate, heated under nitrogen to 50° C., and a small amount of a solution of 49.31 g of 3,3-(2,2-dimethyltrimethylenedioxy)-cis-[bicyclo[3.3.0]octan-7-one in 370 ml of dimethyl carbonate is added thereto. By adding 2 ml of methanol, the reaction is induced; the remainder of the solution is added, and the mixture is stirred a total of 7.5 hours at 50° C. The mixture is cooled in an ice bath, excess sodium hydride is decomposed with methanol, water is added, and the mixture is neutralized with acetic acid. The product is extracted with dichloromethane, concentrated under vacuum, and the product crystallized with hexane, yielding 53.44 g of a product having a melting point of 72° C.

1(b)

7,7-(2,2-Dimethyltrimethylenedioxy)-3α-hydroxy-cis-bicyclo[3.3.0]octane-2β-carboxylic Acid Methyl Ester

Method A

Under heating, 52.0 g of 7,7-(2,2-dimethyltrimethylenedioxy)-cis-bicyclo[3.3.0]octan-3-one-2-carboxylic acid methyl ester is dissolved in 1,000 ml of methanol and cooled to −40° C. Then 20.91 g of sodium borohydride is introduced, the mixture is stirred for 30 minutes, gradually combined with 171 ml of acetone, and neutralized with acetic acid after one additional hour. After removing the main quantity of solvent by distillation, the mixture is combined with water and dichloromethane, the organic phase is dried with sodium sulfate and concentrated under vacuum. The residue is taken up in 550 ml of methanol, 9.94 g of sodium methylate is added, and the mixture is heated for 105 minutes to 40° C. The mixture is cooled in an ice bath, neutralized, and worked up as described above. The resultant crude product is chromatographed on silica gel with dichloromethane-ethyl acetate mixtures, thus obtaining 47 g of the desired compound which can be crystallized with hexane and has a melting point of 43° C.

Method B 56.6 g of 7,7-(2,2-dimethyltrimethylenedioxy)-cis-bicyclo[3.3.0]octan-3-one-2-carboxylic acid methyl ester is dissolved in 300 ml of ethyl acetate and, after addition of 5.1 g of platinum dioxide, hydrogenated at 22° C. under normal pressure until hydrogen absorption is completed. The mixture is filtered off from the catalyst and concentrated under vacuum, yielding 56.8 g of the desired compound as a crude product. The product can be crystallized from hexane, thus obtaining 44.4 g of initial crystallized product, mp 43° C.

1(c)

7,7-(2,2-Dimethyltrimethylenedioxy)-3α-tert-butyldimethylsilyloxy-cis-bicyclo[3.3.0]octane-2β-carboxylic Acid Methyl Ester

8.53 g of 7,7-(2,2-dimethyltrimethylenedioxy)-3α-hydroxy-cis-bicyclo[3.3.0]octane-2β-carboxylic acid methyl ester is dissolved in 9 ml of dimethylformamide; 5.11 g of imidazole and 5.43 g of tert-butyldimethylchlorosilane are added thereto and the mixture stirred for 1.5 hours at 22° C. The mixture is combined with diethyl ether and sodium chloride solution; the ether phase is washed with cold, 1N sulfuric acid, sodium bicarbonate solution and sodium chloride solution, dried with sodium sulfate, and concentrated under vacuum, thus obtaining 12.17 g of product, adequately pure for further reaction.

1(d)

7,7-(2,2-Dimethyltrimethylenedioxy)-3α-tert-butyldimethylsilyloxy-cis-bicyclo[3.3.0]octane-2β-carboxylic Acid

9.54 g of 7,7-(2,2-dimethyltrimethylenedioxy)-3α-tert-butyldimethylsilyloxy-cis-bicyclo[3.3.0]octane-2β-carboxylic acid methyl ester is dissolved in 50 ml of methanol and 26 ml of 5% strength sodium hydroxide solution and heated under reflux for 1.5 hours, then concentrated under vacuum, diluted with water, and neutral compounds are removed by extraction with diethyl ether. The mixture is cooled in an ice bath, combined with 2N sulfuric acid until a pH of 3 is attained, extracted with diethyl ether, dried with calcium sulfate, and concentrated under vacuum, thus obtaining 9.2 g of a crystalline product which is of adequate purity for further reaction.

We claim:

1. A process for the manufacture of an optically active cis-bicyclo[3.3.0]octane-2-aldehyde of Formula I

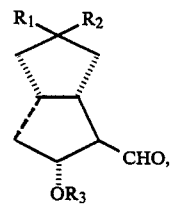

wherein
$R_1$ and $R_2$ jointly represent —O—X—O— where x is straight-chain or branched-chain alkylene of 1–7 carbon atoms, or
$R_1$ and $R_2$ individually represent the residue OR where R is straight-chain or branched-chain alkyl of 1–7 carbon atoms, and
$R_3$ is hydrogen, alkyl of 1–7 carbon atoms, aralkyl of 7–10 carbon atoms, tetrahydropyranyl, trialkylsilyl of 1–6 carbon atoms in the alkyl, which alkyl can also be substituted by phenyl, or dialkylphenylsilyl or alkyldiphenylsilyl each of 1–16 carbon atoms in the alkyl, comprising separating diastereomeric amides of Formula II

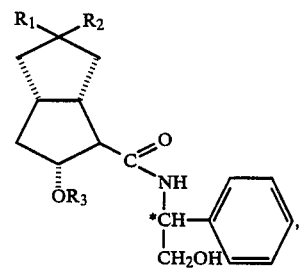

wherein $R_1$, $R_2$ and $R_3$ have the meanings set forth above, and reducing the thus-obtained enantiomerically pure amide of Formula II to form said optically active compound of Formula I.

2. A process of claim 1, wherein the separating step is column chromatography.

3. A process of claim 2, wherein the column chromatography is performed on silica gel.

4. A process of claim 2, wherein the column chromatography is performed on aluminum oxide.

5. A process of claim 1, wherein the separation step is fractional crystallization.

6. A process of claim 1, wherein the reduction is performed by diisobutyl aluminum hydride.

7. A process of claim 1, further comprising converting the optically active cis-bicyclo[3,3,0]octane-2-aldehyde of Formula I into iloprost.

* * * * *